United States Patent [19]

Iwatschenko et al.

[11] Patent Number: 4,811,928
[45] Date of Patent: Mar. 14, 1989

[54] CONTROL CLAMP FOR INFUSION HOSES

[75] Inventors: Peter Iwatschenko; Wolfgang Wolkenströrfer, both of Neunkirchen; Wolfgang Hofmann, Heroldsbach; Walter Prell, Hallerndorf, all of Fed. Rep. of Germany

[73] Assignee: Pfrimmer-Viggo GmbH & Co. KG, Erlangen, Fed. Rep. of Germany

[21] Appl. No.: 93,527

[22] PCT Filed: Dec. 3, 1986

[86] PCT No.: PCT/EP86/00701
§ 371 Date: Jul. 31, 1987
§ 102(e) Date: Jul. 31, 1987

[87] PCT Pub. No.: WO87/03493
PCT Pub. Date: Jun. 18, 1987

[30] Foreign Application Priority Data

Dec. 4, 1985 [DE] Fed. Rep. of Germany ....... 3542899

[51] Int. Cl.⁴ .............................................. F16K 7/06
[52] U.S. Cl. ............................................ 251/7; 251/4
[58] Field of Search ............................. 251/4, 7

[56] References Cited

U.S. PATENT DOCUMENTS

| | | | |
|---|---|---|---|
| 2,819,864 | 1/1958 | Marks | 251/7 |
| 3,254,869 | 6/1906 | Easey | 251/4 |
| 3,818,945 | 6/1974 | Bittner et al. | |
| 3,920,215 | 11/1975 | Knauf | 251/7 |
| 4,047,694 | 9/1977 | Adelberg | |
| 4,582,292 | 4/1986 | Glatzbach et al. | 251/4 X |

FOREIGN PATENT DOCUMENTS 59025 2/1938 Norway .

*Primary Examiner*—A. Michael Chambers
*Assistant Examiner*—John C. Fox
*Attorney, Agent, or Firm*—Brumbaugh, Graves, Donohue & Raymond

[57] ABSTRACT

A control clamp for adjusting the flow rate of a liquid through a flexible hose, such as the hose of an infusion device is provided with a manually operable means for varying the flow cross section of the hose. The means comprises three clamping jaws (14,14',14") of circular sector shape, in section perpendicular to the longitudinal axis of the hose (10), the relative spacing between the clamping jaws being variable by moving them along radii (16,16',16") which intersect the longitudinal axis (20).

8 Claims, 2 Drawing Sheets

CONTROL CLAMP FOR INFUSION HOSES

BACKGROUND OF THE INVENTION

The invention relates to a control clamp for adjusting the flow rate of a liquid through a flexible hose, such as the hose of an infusion device, comprising a means for varying the flow cross section.

Such control clamps are known, for instance, from DE-OS No. 20 43 551, DE-PS No. 22 42 539, DE-OS No. 27 41 594, and U.S. Pat. No. 3,215,395.

Packages for one-time use have become widely accepted in the parenteral administration of liquids by infusion or transfusion devices. Such packages usually contain a hose of flexible material, such as polyvinylchloride, PVC, and a control clamp by means of which the flow cross section of the hose can be varied to adjust the velocity of flow of the liquid as desired. Typical flow velocities are from 50 to 120 ml/h which corresponds to about 25 to 60 drops/min. With known control clamps such flow velocities are adjusted by squeezing the hose by way of the control clamp until it has a gap width of approximately 4/100 mm.

Once the flow velocity has been adjusted for a liquid to be administered parenterally, it should not change involuntarily. Yet the hoses in question, particularly those made of PVC, as is well-known, have the property of becoming deformed plastically under pressure. This so-called "cold flow" of the plastic material in the long run results in a change of the flow cross section so that the required constant nature of the flow velocity cannot be assured.

DE-OS No. 20 43 541 already has for its object the provision of a control clamp with which cold flow is avoided. In his younger DE-OS No. 26 53 515, the same applicant confirms on page 4, line 6, that this aim has not been fully reached in that case.

According to German Pat. No. 22 42 539 the cold flow of the hose material is to be prevented by the asymmetric provision of a recess at one side of a clamping face. Into this recess a so-called excess of the hose is formed during squeezing, and it remains largely free of mechanical forces which might change its shape, even in clamped condition. For this reason it is said not to have any cold flow.

The flow velocity of the parenterally administered liquid is influenced not only by the flow cross section of the hose but by other parameters as well, such as the pressure conditions prevailing at both ends of the hose. Critical in this context are particularly pressure variations at the patient end as they may cause undesirable changes in the flow conditions. The known control clamps essentially adjust the flow cross section of the hose in a strictly limited range only. As a consequence of this "point action" of the known control clamps any pressure variation without dampening at the patient end directly changes the flow conditions, whereby the flow velocity varies undesirably.

Limiting the clamping action to a rather short hose section has another disadvantageous consequence in that the flow cross section may be altered by tensile forces acting in longitudinal direction of the hose.

U.S. Pat. No. 3,215,395 describes a control clamp which may serve to squeeze a certain length of hose. Yet the length of the distance in that case is limited by the circumference of a clamping roll of polygonal shape. Moreover, the clamping roll described requires some skill on the part of the user and, obviously, does not prevent cold flow.

It is the object of the invention to design a control clamp of the generic kind in question such that, whil preventing cold flow, the flow velocity of the liquid through the flexible hose remains constant, once adjusted, and is also largely uninfluenced by pressure variations at the patient end.

SUMMARY OF THE INVENTION

This object is met, in accordance with the invention, in that the control clamp is provided with a means for varying the flow cross section, which means comprises at least three clamping jaws between which the hose is clamped and between which the relative spacing is variable.

While the state of the art provides for only two clamping members to be displaced with respect to each other, the invention provides for at least and preferably three clamping jaws which clamp the hose between them.

The spacing of the three clamping jaws is adjustable manually to alter the flow cross section.

In a preferred modification of the invention the three clamping jaws are configured at least approximately like circular sectors in sectional elevation perpendicular to the longitudinal axis of the hose, and they each have the same shape.

In the case of a preferred modification of the invention the three clamping jaws of circular sector shape are displaceable along radii intersecting the longitudinal axis of the hose such that the central edges of the clamping jaws are movable on the three radii in a direction toward the longitudinal axis of the hose. Hereby they squeeze the hose laterally into free spaces between the clamping jaws whereby the hose is deformed such that the walls of the hose largely abut each other in parallel planes and the cross section remaining free assumes at least approximately the configuration of a triangle having concavely curved sides.

A relatively long portion of the hose may be narrowed uniformly by the control clamp according to the invention because the clamping jaws are adapted to clamp the hose for a longer distance of, for instance, 2 to 5 cm.

In cross section a rotationally symmetrical clamping state of the hose thus is obtained, with those portions of the wall of the hose subjected to strong bending or deforming forces being far remote from those wall portions which define the flow cross section. The latter wall portions, therefore, will not change in shape even in clamped condition so that the flow cross section remains constant.

In an advantageous further development of the invention the clamping jaws of circular sector shape define a circular cylinder or cone so that they can be pressed together by means of an outer sleeve. To this end the clamping jaws preferably are provided with an external thread and the sleeve is provided with an internal thread, the sleeve and the clamping jaws being formed conically in opposite directions.

It is likewise conceivable to press the clamping jaws together symmetrically by means of a hose clamp.

In accordance with a preferred further development of the invention a centering insert is provided between the clamping jaws in order that the hose may be squeezed in rotational symmetry with respect to its longitudinal axis between the clamping jaws (in the case of three clamping jaws at an angle of rotation of 120°). Equal hose sections thus are clamped in each of the free spaces between the clamping jaws.

For centering, the hose also may be preshaped triangularly.

It is likewise possible to adjust the relative spacing of the clamping jaws by means of a connecting link guide means as is customary with conventional control clamps.

BRIEF DESCRIPTION OF THE DRAWINGS

An embodiment of the invention will be described in greater detail below, with reference to the drawing, in which.

DETAILED DESCRIPTION OF THE PREFERRED EMBODIMENT

Figure 1:
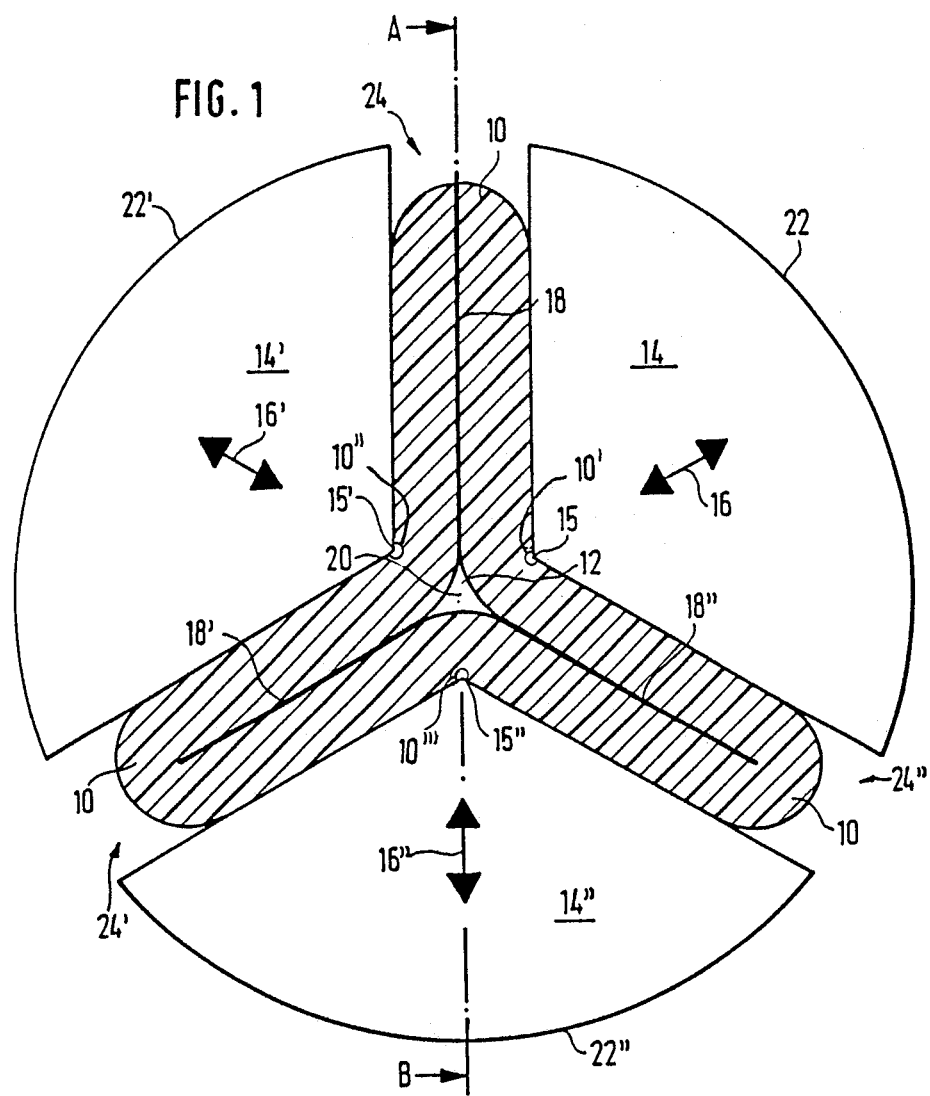
FIG. 1 is a sectional elevation of the clamping jaws and the clamped hose.

With reference to FIG. 1 the hose 10 made of PVC is narrowed down by the clamping jaws 14,14',14" to flow cross section 12. To this end the clamping jaws each are displaceable in the direction of the arrows along radii 16,16',16". The central edges 15,15',15" of the clamping jaws 14,14', 14" of circular sector shape move on the radii 16,16',16" so that the hose 10 is caused to assume a rotationally symmetrical clamping state with respect to its longitudinal axis 20. As shown in FIG. 1, the inner walls of the hose 10 along abutting surfaces 18,18',18" largely lie in parallel planes and close to each other so that what remains free is only the flow cross section 12 which is triangular in section and has concave side faces.

The peripheral portions 22,22',22" of the clamping jaws 14, 14', 14" at least approximately constitute a cylinder or cone. With reference to FIG. 1, free spaces 24,25',24" remain between the clamping jaws, the hose 10 being clamped partly in each of them.

Figure 2:
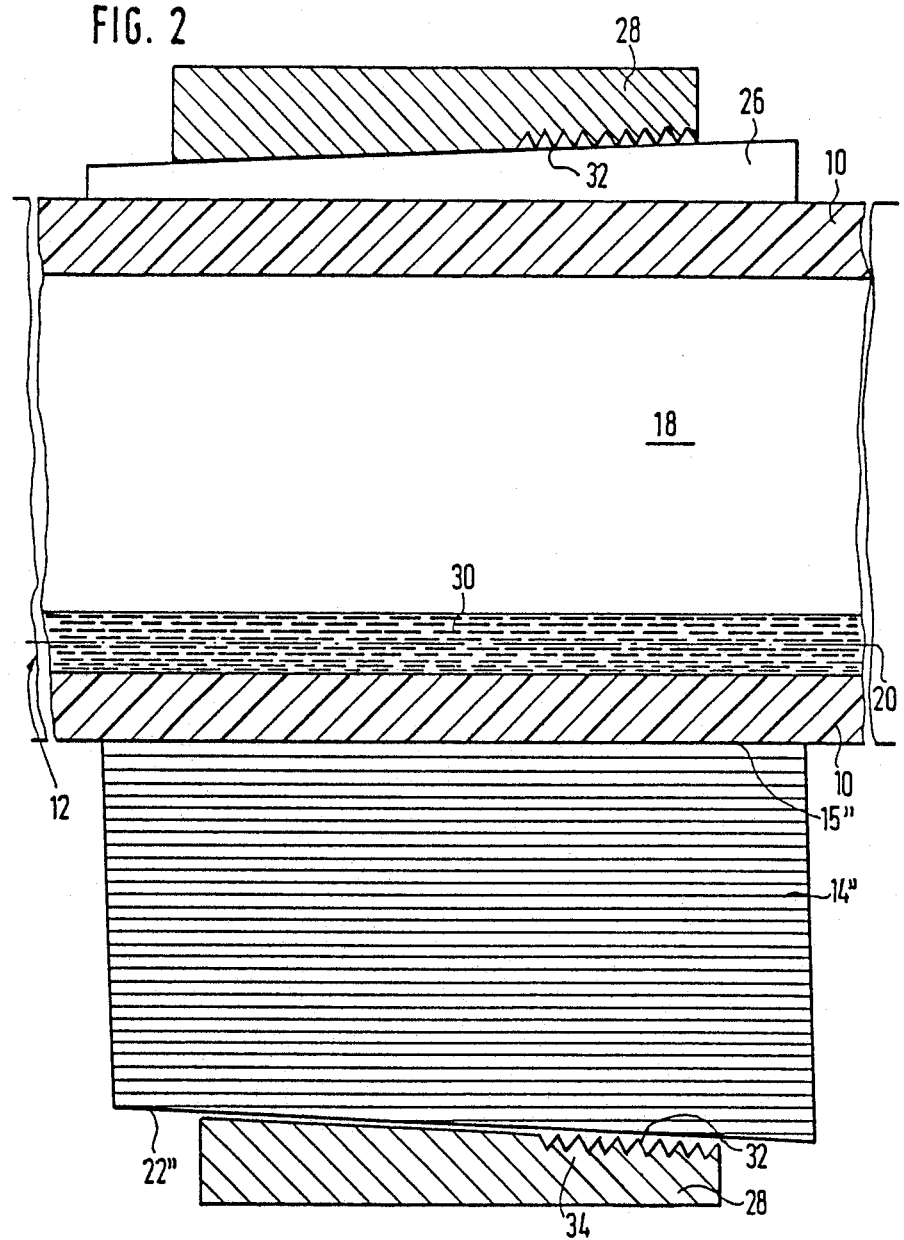
FIG. 2 is a sectional elevation along line A—B in FIG. 1.

FIG. 2 shows the section along line A—B in FIG. 1. In addition to the structural members shown in FIG. 1, a centering insert 26 and an outer sleeve 28 are provided. The centering insert 26 is provided in each of the free spaces 24,24',24" between the clamping jaws and has the effect that portions of equal length of the hose 10 are squeezed in the free spaces 24,24',24". At the outside, the centering inserts 26 are flush with the peripheral portions 22, 22',22" of the clamping jaws, supplementing them at least approximately to a full circle (not shown).

The centering insert may be dispensed with in particular if the hose 10 is preformed at least in the range of the clamping jaws 14,14',14" such that the edges 15,15',15" of the clamping jaws positively engage the hose 10 in rotational symmetry at an angle of rotation of 120°. To accomplish that, the hose 10 is preformed plastically from the beginning approximately into triangular shape in the area of the control clamp. And it comprises three guide grooves 10', 10", 10''' which extend parallel to the longitudinal axis 20 and into which the sharp edges 15,15',15" of the clamping jaws engage in such manner that identical hose sections each are clamped in the free spaces 24,24',24".

In the case of the embodiment shown in FIG. 2 the clamping jaws 14,14',14" are moved by means of a sleeve 28 along the radii 16,16',16" which pass through the longitudinal axis 20 of the hose 10. To this end the outer peripheral portions 22,22',22" of the clamping jaws are provided with an external thread 32 and the inner circumference of the sleeve 28 is provided with an internal thread 34. The flow cross section 12 of the hose 10 thus is varied and the flow velocity of the liquid 30 controlled in response to the state of the threaded connection between sleeve and clamping jaws.

As shown in FIG. 2, the sharp edges 15,15',15" of the clamping jaws extend at least approximately parallel to the longitudinal axis 20 of the hose 10. Thus a relatively long hose section of, for instance, 2 to 5 cm may be clamped, and the throttling of the flow velocity by the control clamp provides good dampening. In other words, pressure variations at the patient end are transmitted to the other end of the control clamp upon strong dampening only so that the flow velocity does not differ at once from the rated value if there are brief pressure variations at the patient end.

What is claimed is:

1. A control clamp for adjusting flow rate of a liquid through a flexible hose of an infusion device having a longitudinal axis comprising
at least three clamping jaws of variable relative spacing between which the hose is clamped, each of said clamping jaws being displaceable along radii which intersect the longitudinal axis of the hose and having sharp edges that extend parallel to said longitudinal axis, lie on said radii and engage said hose to vary the cross-sectional flow area thereof, and means for moving said clamping jaws such that said edges move along along said radii, said hose having three guide grooves on the outer periphery thereof which extend parallel to said longitudinal axis and which engage with said sharp edges such that the hose can be clamped symmetrically between the clamping jaws.

2. The control clamp according to claim 1 wherein there are free spaces provided between the clamping jaws laterally with respect to the direction of movement thereof, the hose being deformable into the free spaces such that the walls of the hose substantially abut each other in parallel planes, and the cross-sectional flow area of the hose is in the shape of a three-point star.

3. The control clamp according to claim 2 wherein the clamping jaws clamp the hose in parallel for a distance of from 1 to 50 mm.

4. The control clamp according to claim 1 wherein the clamp comprises four clamping jaws.

5. The control clamp according to claim 4 further comprising a centering insert for the hose provided between the clamping jaws for symmetrically guiding the hose with respect to the clamping jaws.

6. The control clamp according to claims 1 or 4 wherein said means for moving said clamping jaws are manual means.

7. The control clamp according to claims 1 or 4 wherein the clamping jaws are approximately of circular sector shape in a section perpendicular to the longitudinal axis of the hose.

8. The control clamp according to claims 1 or 4 wherein an outer surface of the clamping jaws lie proximately on the periphery of a cone and said moving means includes a sleeve which embraces the clamping jaws said clamping jaws being provided with an external thread and the sleeve is provided with an internal thread and wherein the sleeve and the clamping jaws are shaped conically in opposite directions.

* * * * *